US012390188B2

(12) United States Patent
Teixeira Dos Santos Paulo

(10) Patent No.: US 12,390,188 B2
(45) Date of Patent: Aug. 19, 2025

(54) DEVICE FOR INTRA-CARDIAC AND INTRA-VASCULAR SURGICAL PROCEDURE HAVING AN ENDOLUMINAL ULTRASOUND PROBE

(71) Applicant: Nelson Jorge Teixeira Dos Santos Paulo, Arcozelo VNG (PT)

(72) Inventor: Nelson Jorge Teixeira Dos Santos Paulo, Arcozelo VNG (PT)

( * ) Notice: Subject to any disclaimer, the term of this patent is extended or adjusted under 35 U.S.C. 154(b) by 2042 days.

(21) Appl. No.: 15/565,301

(22) PCT Filed: Apr. 13, 2016

(86) PCT No.: PCT/IB2016/052106
§ 371 (c)(1),
(2) Date: Oct. 9, 2017

(87) PCT Pub. No.: WO2016/166681
PCT Pub. Date: Oct. 20, 2016

(65) Prior Publication Data
US 2018/0055347 A1   Mar. 1, 2018

(30) Foreign Application Priority Data

Apr. 13, 2015  (PT) .......................................... 108357
Nov. 30, 2015  (PT) .......................................... 108996

(51) Int. Cl.
*A61B 8/12*   (2006.01)
*A61B 8/00*   (2006.01)
(Continued)

(52) U.S. Cl.
CPC ................ *A61B 8/12* (2013.01); *A61B 8/445* (2013.01); *A61B 8/4494* (2013.01); *A61B 8/466* (2013.01);
(Continued)

(58) Field of Classification Search
None
See application file for complete search history.

(56) References Cited

U.S. PATENT DOCUMENTS 5,166,787 A * 11/1992  Irion .................. A61B 1/00181
                                                              348/75
6,547,739 B2 * 4/2003  Jordfald .................... A61B 8/12
                                                              600/121
(Continued)

*Primary Examiner* — Luther Behringer
(74) *Attorney, Agent, or Firm* — Leason Ellis LLP

(57) ABSTRACT

Device for intra-cardiac and intra-vascular surgical procedure comprising an endoluminal ultrasound catheter probe which comprises a flexible tube a working channel for receiving and guiding transcatheter devices or instruments for the surgical procedure, and a three-dimension ultrasonic transducer, wherein the flexible tube has a working channel outlet on the distal end defining a ring-shaped surface, wherein the working channel longitudinal axis is off-centred in respect of the flexible tube longitudinal axis, thus defining a wider section and a narrower section of said ring-shaped surface, wherein the ultrasonic transducer is placed or coupled to the wider section. An embodiment comprises a hatch door for opening and closing the outlet, the hatch door being coupled to said wider section by a hinge, wherein the ultrasonic transducer is placed at said hatch door and the hatch door is hinged to rotate about an axis parallel to the longitudinal axis of the flexible tube.

20 Claims, 11 Drawing Sheets

(51) Int. Cl.
  *A61B 17/34*  (2006.01)
  *A61B 90/00*  (2016.01)
  *A61B 17/00*  (2006.01)

(52) U.S. Cl.
  CPC ............... *A61B 8/467* (2013.01); *A61B 8/52* (2013.01); *A61B 17/3421* (2013.01); *A61B 90/37* (2016.02); *A61B 2017/00243* (2013.01); *A61B 2017/00292* (2013.01); *A61B 2017/00314* (2013.01); *A61B 2017/00323* (2013.01); *A61B 2017/0034* (2013.01); *A61B 2090/3782* (2016.02); *A61B 2090/3784* (2016.02)

(56) References Cited

U.S. PATENT DOCUMENTS

| | | | | |
|---|---|---|---|---|
| 8,088,065 B2* | 1/2012 | Karasawa | ............ | A61B 1/3132 600/157 |
| 9,955,946 B2* | 5/2018 | Miller | .................. | A61B 8/0841 |
| 2002/0095088 A1* | 7/2002 | Jordfald | .................. | A61B 8/12 600/462 |
| 2004/0068191 A1 | 4/2004 | Seward et al. | | |
| 2008/0287862 A1* | 11/2008 | Weitzner | ................ | A61B 34/71 604/28 |
| 2009/0259097 A1 | 10/2009 | Thompson et al. | | |
| 2010/0145306 A1 | 6/2010 | Mickley et al. | | |
| 2010/0249502 A1* | 9/2010 | Karasawa | ........... | A61B 1/3132 600/109 |
| 2010/0249512 A1 | 9/2010 | McKinley et al. | | |
| 2010/0280316 A1 | 11/2010 | Dietz et al. | | |
| 2011/0021926 A1* | 1/2011 | Spencer | ............... | A61B 5/0062 600/478 |
| 2011/0166455 A1* | 7/2011 | Cully | .................. | A61B 8/4466 600/463 |
| 2011/0319989 A1* | 12/2011 | Lane | .................... | A61F 2/2409 623/2.11 |
| 2013/0128702 A1 | 5/2013 | Degertekin et al. | | |
| 2014/0135685 A1 | 5/2014 | Kabe et al. | | |
| 2014/0222043 A1 | 8/2014 | Snow et al. | | |
| 2014/0378772 A1 | 12/2014 | Sundt, III et al. | | |
| 2015/0257779 A1* | 9/2015 | Sinelnikov | ............... | A61B 8/12 600/439 |

\* cited by examiner

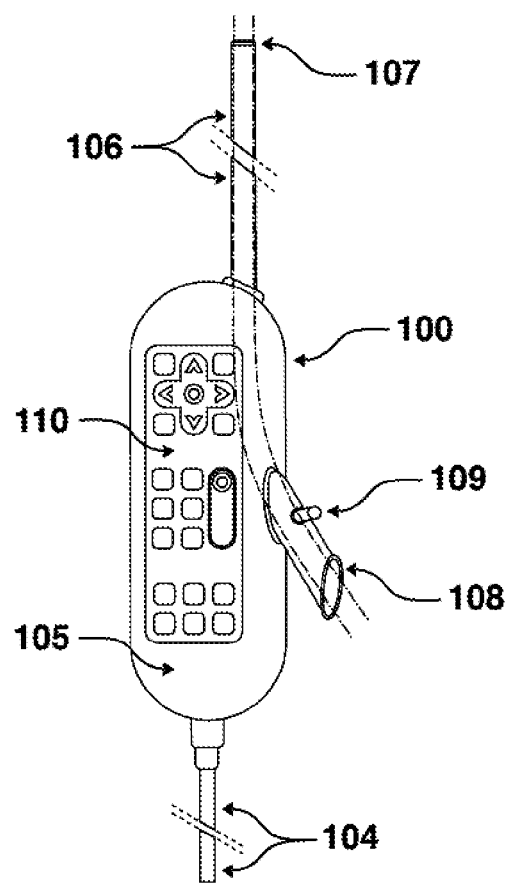
Fig. 3
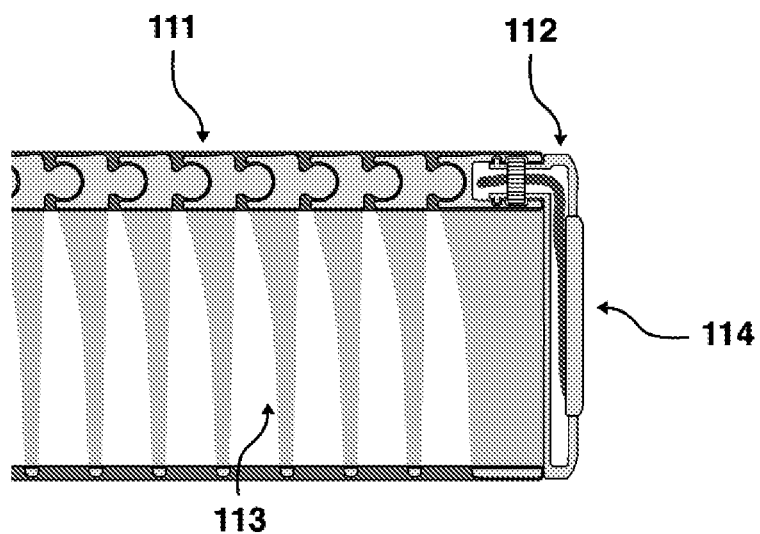
Fig. 4.1

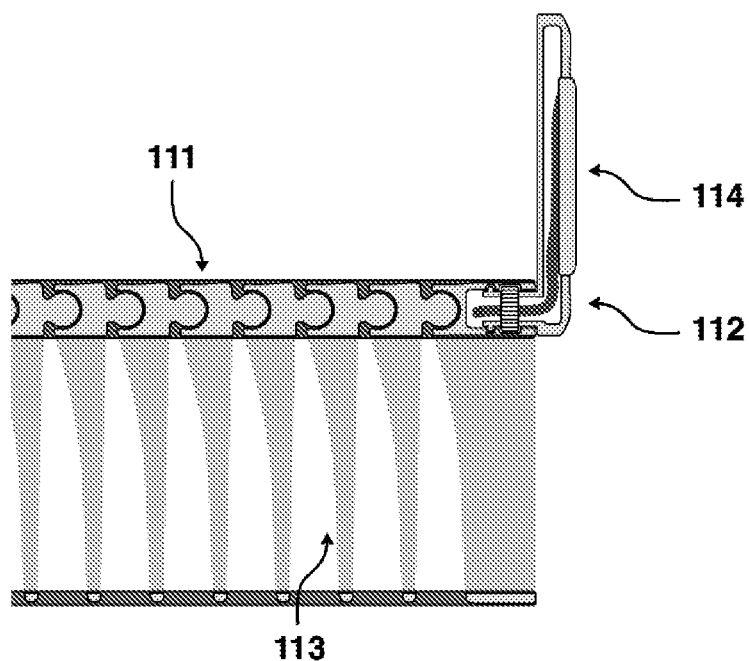
Fig. 4.2
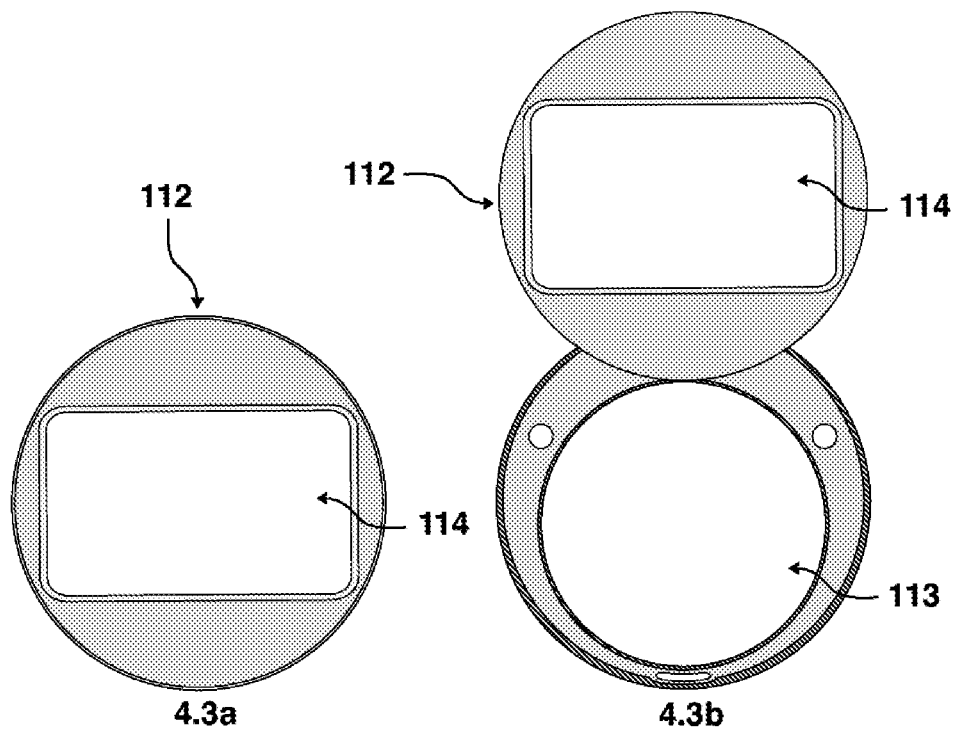
Fig. 4.3

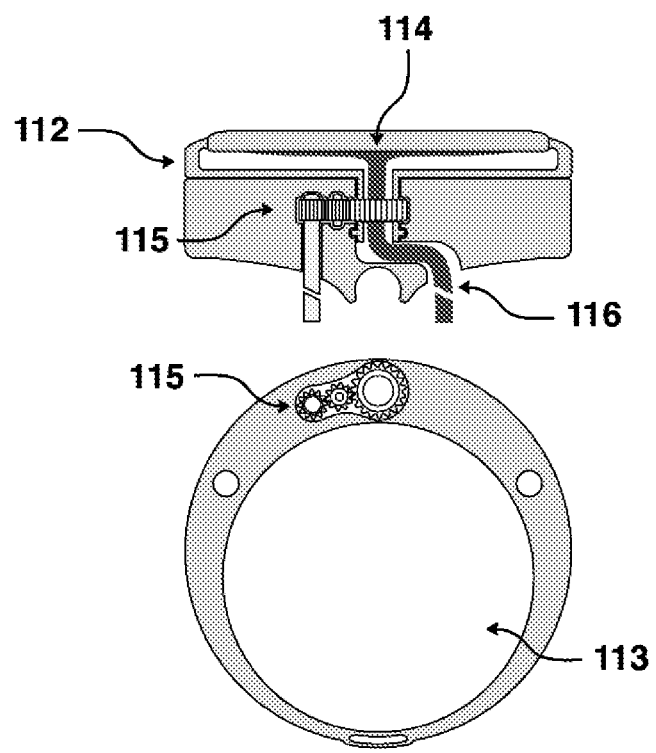
Fig. 4.4
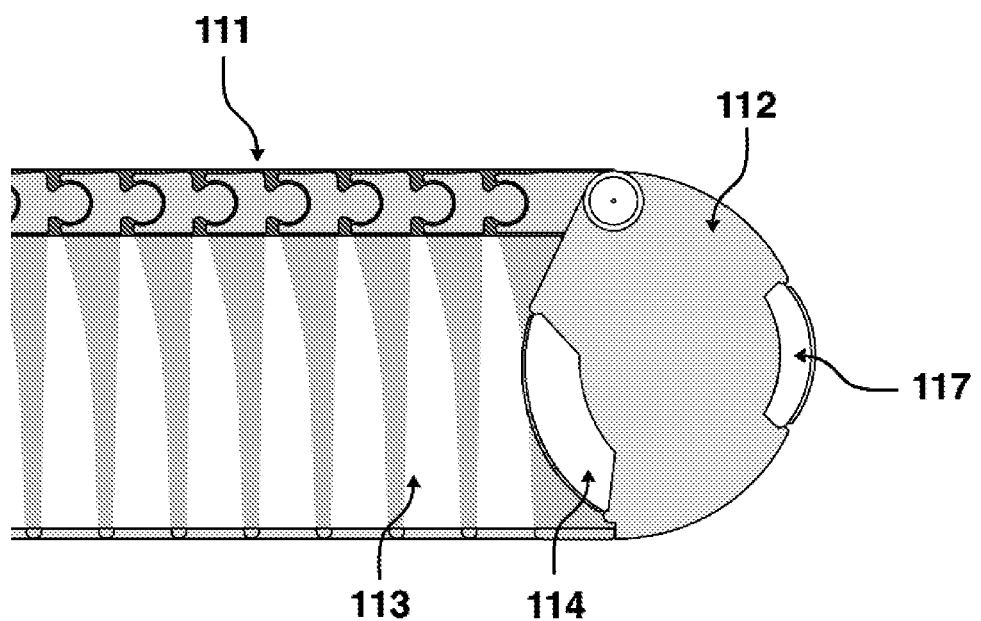
Fig. 4.5

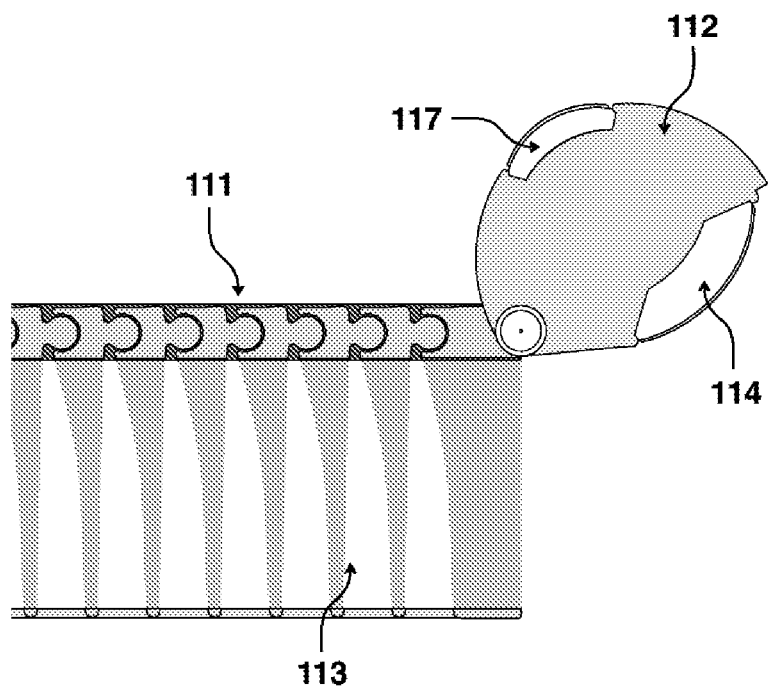
Fig. 4.6
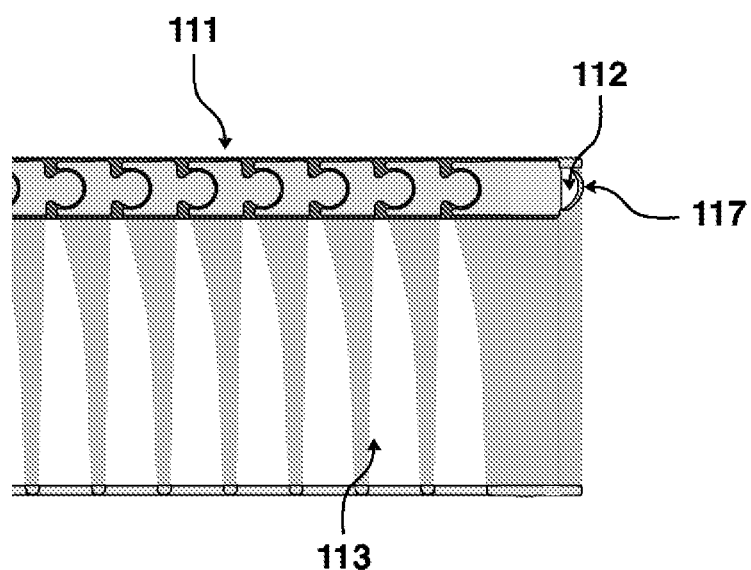
Fig. 4.7

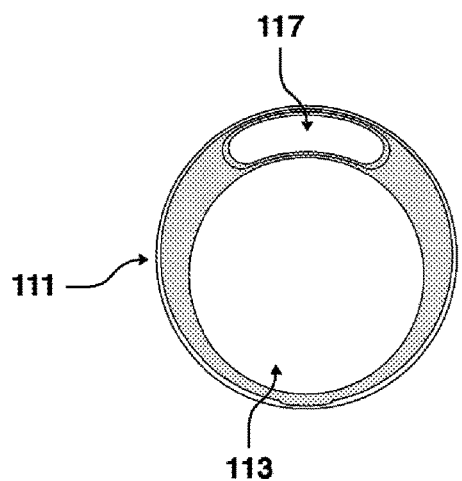
Fig. 4.8
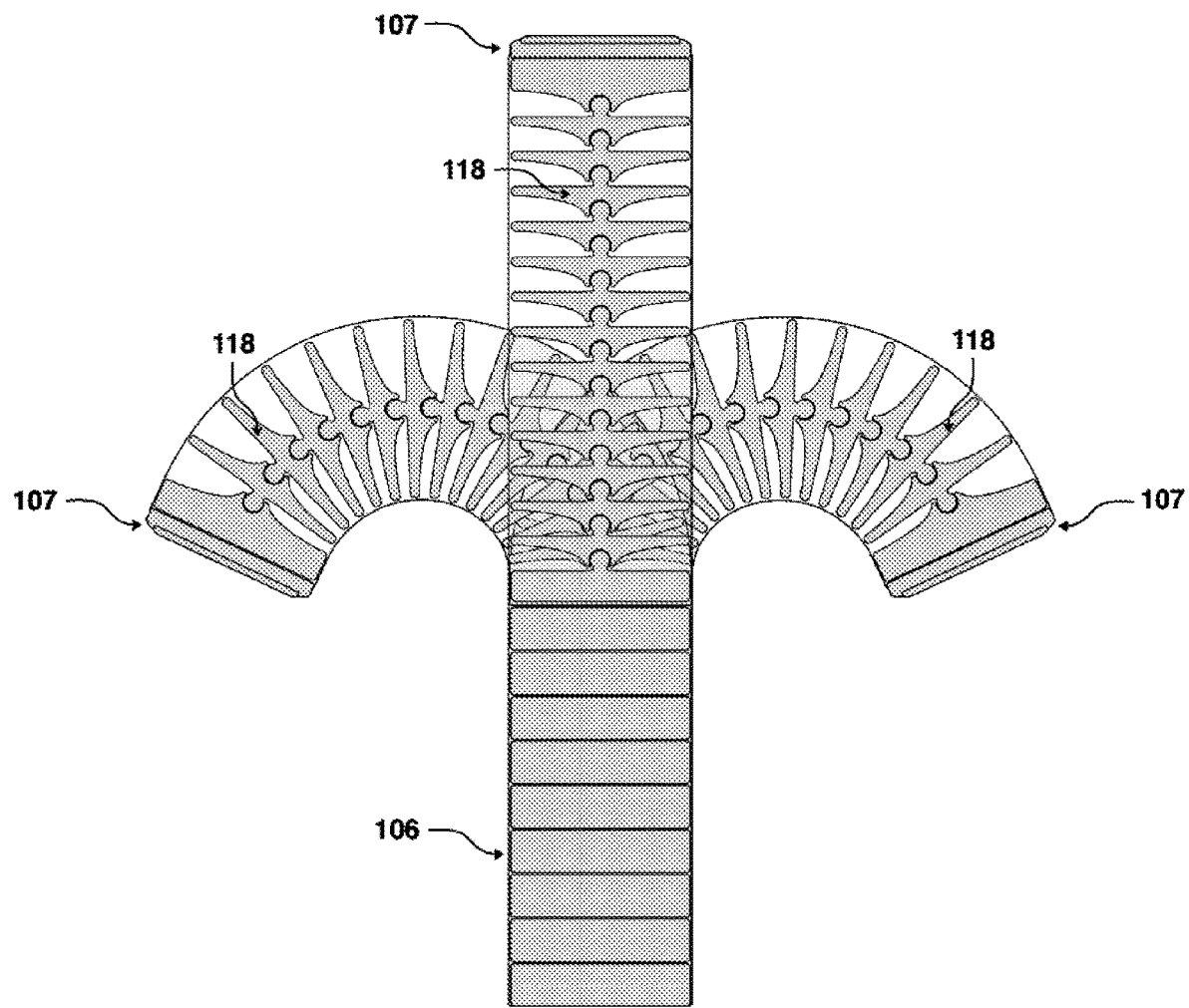
Fig. 5

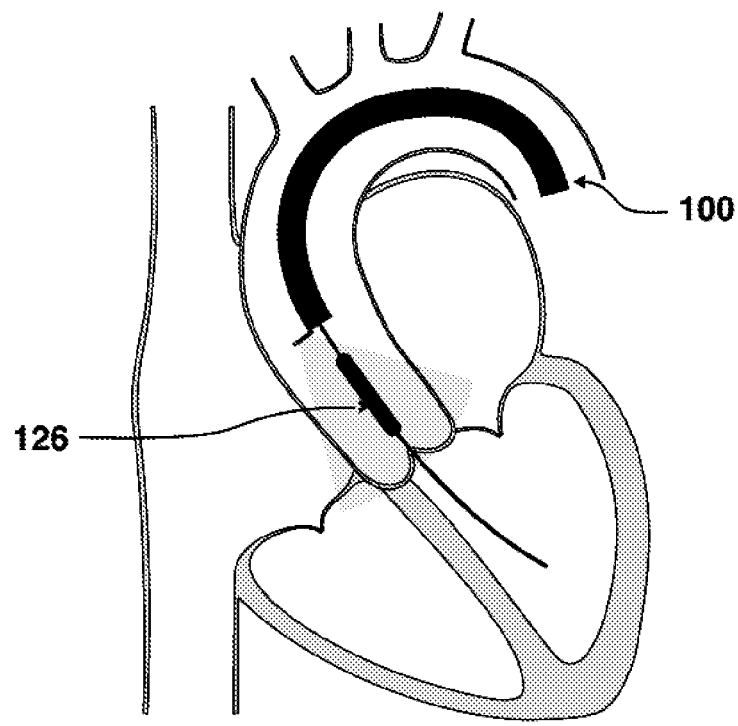
Fig. 8.1
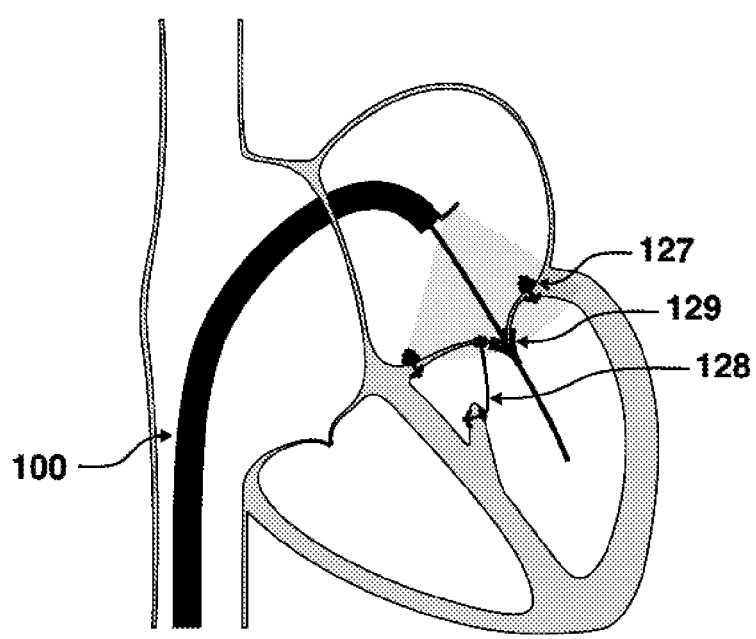
Fig. 8.2

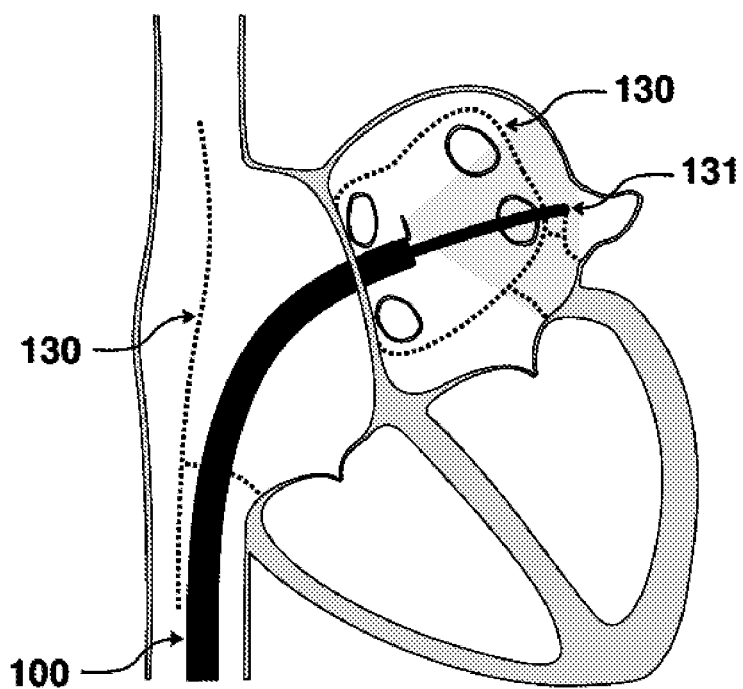
Fig. 8.3
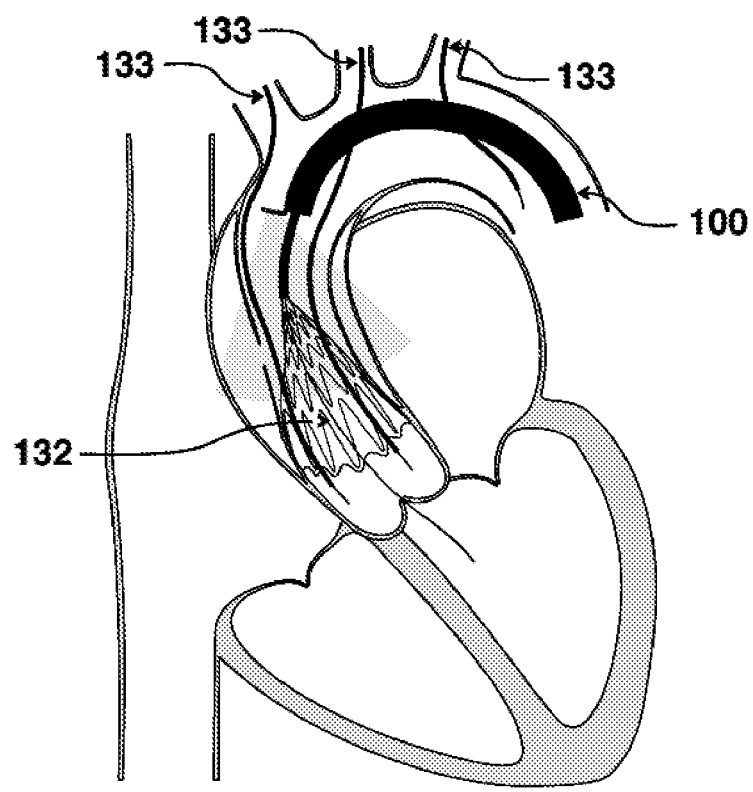
Fig. 8.4

DEVICE FOR INTRA-CARDIAC AND INTRA-VASCULAR SURGICAL PROCEDURE HAVING AN ENDOLUMINAL ULTRASOUND PROBE

CROSS-REFERENCE TO RELATED APPLICATIONS

This application is a U.S. National Stage Application under 35 U.S.C. § 371 of International Patent Application No. PCT/IB2016/052106, filed Apr. 13, 2016 which claims priority to Portugal Application No. 108996, filed Nov. 30, 2015 and Portugal Application No. 108357, filed Apr. 13, 2015, which are hereby incorporated by reference in their respective entireties.

TECHNICAL FIELD

The present disclosure relates to a device for intra-cardiac and intra-vascular surgical procedure with beating heart, for catheter based and complex surgical procedures on beating heart and blood filled vessels. The device comprises an endoluminal ultrasound probe having a working channel for catheter based devices and specially designed surgical instruments, that can be introduced in the patient major peripheral arteries and veins as vascular port sites, in which the probe distal component is flexible and can be controlled in a wide range of positions to guide and point an ultrasonic transducer and the working channel in anatomic vascular and cardiac structures.

BACKGROUND ART

For intra-cardiac and vascular surgical intervention the heart or vessel must be blood free bypassing the blood thru cardiopulmonary bypass machine for conventional open heart surgery or by cross clamping the vessel for conventional vascular surgery.

The conventional heart and vascular surgery is considerably invasive and is associated with significant morbidity and mortality risk despite the state of the art in such surgical treatments.

The natural history of most heart and vascular diseases is related to degenerative progression, aging and increasing weakness of the anatomical structures. This intrinsic systemic fragility is inherent to all systems and organs adding exceedingly high intervention risk to the conventional surgical intervention that may state as prohibitive.

To prevent the high surgical risk a wide range of minimal invasive intra-cardiac and vascular intervention treatments are known and available but most of these therapeutics options are limited to catheter delivered stent prostheses and devices previously collapsed to an insertion diameter and introduced into a peripheral vessel distant from the diseased vessel or heart structure to treat. These minimal invasive catheter based procedures are performed remotely by indirect vision usually in the hemodynamic laboratory or hybrid operation room using real-time image fluoroscopy or alternatively image echography for guidance and deployment of the stents and devices. The precision for placement and deployment of these devices and stents is paramount, therefore, an accurate dynamic real-time image is mandatory. In addition, in the current state of the art, the real-time image from fluoroscopy is two-dimensional and when assisted with computer tomography or echography for three dimension image the real-time image with direct structure interaction capacity is lost.

Nevertheless these minimally invasive procedures are still very limited in the range of diseases already treated by conventional surgery. Accordingly, for patients that must have a heart or vascular surgical correction but are excessively fragile for conventional surgery and there is no minimally invasive solution available, the disease goes untreated. Consequently, in the field of cardiovascular treatment there is continuous interest and demand for significant development in the field of complex surgical treatment by minimally invasive approaches with reduced procedural risk and improved recovery status. Furthermore, any significant improvement to treat cardiovascular diseases in less complex settings like hemodynamic laboratories and operating rooms to perform complex cardiovascular treatments is warranted.

Accordingly a need exists in the art to allow a trained clinician to perform complex heart and vascular intervention and surgery in a minimally invasive approach and less complex setting.

These facts are disclosed in order to illustrate the technical problem addressed by the present disclosure.

GENERAL DESCRIPTION

A new minimally invasive device for intervention inside the heart and major vessels for catheter based and complex surgical procedures on beating heart and blood filled vessels is disclosed. This device allows a real-time three dimension echography image of the vessels, heart chambers and valves for diagnose and intervention throughout a working channel for catheter based devices and specially designed surgical instruments. The disclosed device has a probe component that can be introduced in the patient major peripheral arteries and veins as vascular port sites in one or more ports depending on the complexity of the procedure. The probe distal component is flexible and can be controlled in a wide range of positions to guide and point the ultrasonic transducer and the working channel in small anatomic vascular and cardiac structures.

The disclosure relates to a device that comprises the capability for real-time three dimension image acquisition for diagnostic, intervention and surgical procedures inside de heart and major vascular vessels thru minimally invasive approach and with beating heart.

Embodiments hereof are directed to a device to access the heart chambers and major vessels in a physiologic blood filed beating heart clinical setup by direct three dimension reconstruction vision through minimally invasive technique for interventional and surgical procedures.

In an embodiment the device comprises two main components, the processor and display unit and the endoluminal probe. The processor and display unit comprises a console unit with a computer module to process the data from the three dimension ultrasonic transducer and a display element to exhibit the real-time three dimension high-resolution images from the ultrasonic transducer. The endoluminal probe has a flexible mechanically controlled cylindrical arm to fit the natural individual vessel and heart anatomy and a hollow hemodynamic valve sealed working channel. The endoluminal and endocardiac images are acquired by a miniaturized three dimension ultrasonic transducer placed at the tip of the endoluminal probe to allow real-time dynamic visualization of the anatomical endovascular or endocardiac structure. The distal component of the probe is flexible and can be controlled in a wide range of positions to guide and point the ultrasonic transducer and the working channel inside the small anatomic vascular and cardiac structures.

The interventional and surgical endovascular and endocardiac manipulation are achieved throughout the hollow hemodynamic valve sealed working channel using the variety of currently available and forthcoming transcatheter devices and specially designed surgical appliances and instruments for cylindrical small caliber working channels. The endoluminal probe is designed for introduction in a major peripheral vessel as vascular access port through a vascular introducer placed by transcutaneous or minimal surgical cut down approach. The peripheral vessels eligible to access with this device may be an artery or a vein suitable to access the anatomical location of the structure to treat. Depending on the complexity of the intended procedure two or more endoluminal probes introduced throughout additional arterial or venous access ports may be required and used at the same time. The more common arteries and veins to access with this device are the femoral vessels, the axillary vessels, the carotid and jugular vessels, although other more central or peripheral vessels may be used. Since the image acquisition of this device is echography based, the use of image fluoroscopy and endovascular contrast is unnecessary, avoiding the radiation exposure, the toxicity of the endovascular contrast and the need for complex settings like hemodynamic laboratory or hybrid operation room. The direct real time three dimension reconstruction vision of this device combined with the direct handling feedback feeling from the structures to treat through the working channel allow to this device a enhanced capability to operate on complex anatomical structures similar to the conventional open surgical field. In addition, the controlled and extraordinary wide flexibility of the distal sensing and interface component of the endoluminal probe allows precise intervention capability that can further be enhanced by the combination of the real time three and two dimension image data collected by the three dimension ultrasonic transducer for more accurate definition of depth, transmurality and limits of the anatomical structures. Likewise, the three dimension ultrasonic transducer additionally allows real time Doppler ultrasound image for diagnostic and procedural end result evaluation. Furthermore, this device may allow a fully percutaneous alternative for previously exclusive surgical option procedures and depending on the complexity of the procedure intended this device can be operated throughout the entire procedure by a skilled clinician without specific or extensive surgical training.

The design of the device enables a significantly larger working channel opening diameter in relation to the outer diameter of the probe. The larger working channel is of utmost importance for the variety of procedures possible with the currently available and forthcoming transcatheter devices and specially designed surgical appliances and instruments for cylindrical small caliber working channels. The larger working channel is also essential for precise tactile feedback from the transcatheter devices and specially designed surgical appliances and instruments when interacting with the vascular and cardiac structures. In particular, a decentralized position of the working channel in relation to the outer ring of the probe is designed to maximize the working channel diameter with the greatest flexibility and tension resistance, in particular in an articulated portion of the flexible mechanically-controlled cylindrical probe.

It is disclosed a device for intra-cardiac and intra-vascular surgical procedure comprising a surgical endoluminal ultrasound probe, said probe comprising:

a flexible tube having a longitudinal hollow which defines a working channel for receiving and guiding transcatheter devices or instruments for the surgical procedure, a hatch door, and a three-dimension ultrasonic transducer, wherein the flexible tube has a working channel outlet on the distal end of the flexible tube, wherein the hatch door is coupled to the distal end of the flexible tube by a hinge for opening and closing the working channel outlet, wherein the ultrasonic transducer is placed at said hatch door.

It is also disclosed a device for intra-cardiac and intra-vascular surgical procedure comprising a surgical endoluminal ultrasound probe, said probe comprising:

a flexible tube having a longitudinal hollow which defines a working channel for receiving and guiding transcatheter devices or instruments for the surgical procedure, and a three-dimension ultrasonic transducer, wherein the flexible tube has a working channel outlet on the distal end of the flexible tube defining a ring-shaped surface, wherein the working channel longitudinal axis is off-centred in respect of the flexible tube longitudinal axis, thus defining two sections of said ring-shaped surface, a wider section and a narrower section, wherein the ultrasonic transducer is placed or coupled to the wider section of the ring-shaped surface.

An embodiment comprises a hatch door for opening and closing the working channel outlet, the hatch door being coupled to said wider section by a hinge, wherein the ultrasonic transducer is placed at said hatch door.

In an embodiment, the hatch door is hinged to rotate about an axis parallel to the longitudinal axis of the flexible tube, in particular the hatch door is hinged to rotate 180° between closed and open positions.

In an embodiment, the ultrasonic transducer is placed at the forward-facing part of the hatch door.

In an embodiment, the hatch door is hinged to rotate about an axis perpendicular to the longitudinal axis of the flexible tube, in particular the hatch door is hinged to rotate between 90° and 180° in respect of the longitudinal axis of the flexible tube between closed and open positions.

In an embodiment, the ultrasonic transducer is placed at the part of the hatch door that is forward-facing when the hatch door is open.

An embodiment comprises a secondary ultrasonic transducer in addition to said ultrasonic transducer herewith main ultrasonic transducer, wherein the secondary ultrasonic transducer is placed at the part of the hatch door that is forward-facing when the hatch door is closed.

In an embodiment, the secondary ultrasonic transducer has a lower definition than the main ultrasonic transducer.

In an embodiment, the flexible tube has the working channel outlet on the distal end of the flexible tube thus defining a ring-shaped surface, wherein the working channel longitudinal axis is off-centred in respect of the flexible tube longitudinal axis, thus defining two sections of said ring-shaped surface, a wider section and a narrower section, wherein the hatch door is placed or coupled to the distal end of the flexible tube at said wider section of the ring-shaped surface.

In an embodiment, the longitudinal hollow is cylindrical.

In an embodiment, the flexible tube is cylindrical.

In an embodiment, the ring-shaped surface is annular and bounded by two non-concentric circles defined respectively by the flexible tube and the longitudinal hollow.

In an embodiment said probe comprises an embedded motor cable for opening or closing the hinge of the hatch door, in particular wherein the embedded motor cable is a rotation motor cable.

An embodiment comprises a wheel gear mechanism for rotational coupling between the rotation motor cable and the hatch door.

It is also disclosed a device for intra-cardiac and intra-vascular surgical procedure comprising a surgical probe, said probe comprising a flexible tube having a longitudinal hollow which defines a working channel for receiving and guiding transcatheter devices or instruments for the surgical procedure, wherein the flexible tube has a working channel outlet on the distal end of the flexible tube defining a ring-shaped surface, and the distal part of the flexible tube comprises a sequential arrangement of a plurality of ring-shaped units along the flexible tube, wherein each unit comprises a ball-joint and is coupled with the adjoining unit or units by said ball-joint.

In an embodiment, the proximal part of the flexible tube is a flexible tube coupled to the most proximal of said units having less flexibility than the sequential arrangement of a plurality of ring-shaped units of the distal part.

In an embodiment, the proximal part of the flexible tube is a polymeric flexible tube coupled to the most proximal of said units.

In an embodiment, the proximal part of the flexible tube is a sequential arrangement of interlocked slidably disposed units, in particular having a lower flexibility than the sequential arrangement of a plurality of ring-shaped units of the distal part of the flexible tube.

In an embodiment, the unit has one or more openings for tunneled passage of embedded motor or electrical cables.

An embodiment comprises one or more embedded motor cables embedded in said openings for axially orienting the distal end of the flexible tube, wherein the embedded motor cable is attached at one of the cable ends to one of said units, in particular wherein the embedded motor cable is attached at one of the cable ends to the most distal unit.

In an embodiment, one of the motor cables is a push-pull motor cable having the tunneled passage opening and attachment placed in the ring-shaped unit opposite the ball-joint placement, in particular the tunneled passage being ribbon-shaped.

In an embodiment, the tunneled passage is an arcuate ribbon-shaped tunneled passage.

In an embodiment, one of the motor cables is a push-pull motor cable having the tunneled passage opening and attachment placed in the ring-shaped unit laterally in respect of the ball-joint placement, in particular the push-pull motor cable having a circular section.

In an embodiment, two of the motor cables are push-pull motor cables having the tunneled passage openings and attachments placed in the ring-shaped unit laterally in respect of the ball-joint placement and opposite in respect of the other cable opening and attachment, in particular the two push-pull motor cables having a circular section.

In an embodiment, the ring-shaped unit has a tapering decreasing thickness in the direction away from the ball-joint.

In an embodiment, the ball-joint of each unit is placed at said wider section of the ring-shaped surface.

In an embodiment, the flexible tube has a working channel inlet on the proximal end of the flexible tube.

An embodiment comprises a handle for the flexible tube on the proximal end of the flexible tube, wherein the working channel inlet is comprised in said handle.

An embodiment of the handle comprises one or more motors for actuating the motor cables, an electronic circuit for controlling said motors and one or more user controls for inputting control of said electronic circuit.

An embodiment comprises a computer for processing data from the ultrasonic transducer and a display for displaying real-time three-dimension images from the ultrasonic transducer.

An embodiment of the handle comprises the terminating connections of the motor and electric cables of the flexible tube.

An embodiment of the handle comprises a valve at the working channel inlet for minimizing blood leaks.

An embodiment of the handle comprises an air removal outlet.

An embodiment of the device comprises an electronic circuit and user controls for inputting control of said electronic circuit, wherein said electronic circuit is for controlling image parameters of the ultrasonic transducer placed at the distal end of the flexible tube and/or for controlling the flexibility of the distal end of the flexible tube.

Ring-shaped surface means a surface that is a flattened ring or loop, wherein the ring may be circular, oval, stadium-shaped, or even other shapes regular or irregular.

Annular surface means a surface bounded by two non-intersecting circles, concentric or non-concentric (i.e. the width of the surface is not constant).

The hatch door is a door that closes the working channel outlet in such a way to minimise intra-cardiac or intra-vascular damage. When closed, it may, or may not, enclose the outlet working channel in a fluid-tight way.

Forward-facing in respect of the endoluminal probe means towards the region where the intervention is to be carried out, i.e. in the direction beyond the distal end of the flexible tube.

A rotation motor cable is a cable able to transmit motion by its own rotation. The rotation motor cable may have an outer sheathing, which preferably does not rotate. A rotation motor cable is preferably circular. A push-pull motor cable is a cable able to transmit motion by its pulling.

A pull motor cable may have an outer sheathing, which preferably does not pull. A push-pull motor cable may have a circular section or be ribbon-shaped. A push-pull motor cable may also be able to transmit motion by its pushing. Also, the outer sheathing preferably does not push.

A section is any of the more or less distinct parts into which something is or may be divided or from which it is made up. In particular, wherein the working channel longitudinal axis is off-centred in respect of the flexible tube longitudinal axis, thus defining two sections of said ring-shaped surface, a wider section and a narrower section, these sections are the two parts of the ring-shaped surface into which the ring-shaped surface may be divided, one having a wider section than the other.

BRIEF DESCRIPTION OF THE DRAWINGS

The following figures provide preferred embodiments for illustrating the description and should not be seen as limiting the scope of disclosure. Drawings are not necessarily to scale.

FIG. 3 is a schematic illustration of a top view of an embodiment of the operating control element and its components.

FIG. 4 is a schematic illustration of embodiments of the probe sensing and interface element and its components.

FIG. 5-6 is a schematic illustration to represent the degree of orientation of the distal segment of an embodiment of the endoluminal probe in the horizontal and vertical axis.

FIG. 8 is a schematic illustration of an embodiment of device in four potential intervention and surgical clinical scenarios.

DETAILED DESCRIPTION

Specific embodiments of the present disclosure are now described with reference to the figures, wherein like reference numbers indicate identical or functionally similar elements.

Although the description of embodiments hereof is in the context of minimally invasive interventional and surgical procedures in the heart and major vessels, the disclosure may be adapted to be used for other concurrent vascular and cardiac diagnostic and therapeutic procedures where it is deemed useful.

The terms "Doppler", "transcatheter aortic valve", "transcatheter mitral valve", "neocordae", "edge-to-edge stitch", "endoprosthesis stent", "sandwich technic", "rapid pacing stimulation", "extracorporeal membrane oxygenator (ECMO)" and "mini-extracorporeal circulation (MECC)" are used in the following description concerning medical devices, surgical techniques, interventional techniques, methods and apparatus according to the published literature and are used as exemplary references.

Examples of materials that may be used in the components of the described device are those that may be normally used to improve the performance of the various components according to the state of the art of the available materials.

Embodiments hereof are related to a device to access the heart chambers and major vessels in a physiologic blood filed beating heart clinical setup by direct three dimensional reconstruction vision through minimally invasive technique for interventional and surgical procedures. All the figures are schematic not to scale illustrations of the described device as the materials, shape and relative size of all components and diagrams may vary accordingly to the desired functionality.

Figure 1:
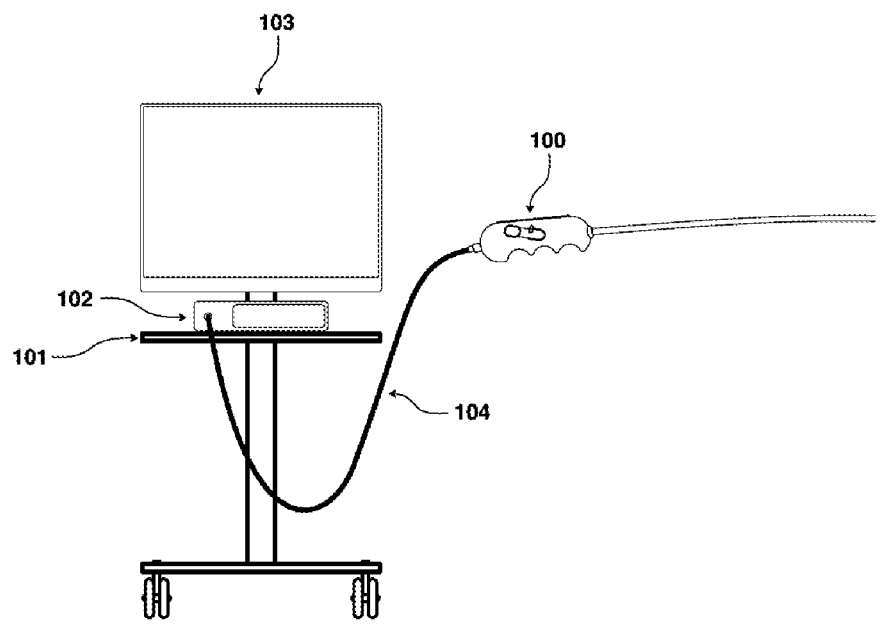
FIG. 1 is a schematic illustration of an embodiment of the device and its components.

FIG. 1 is a schematic illustration of the endoluminal probe 100, the connecting cable 104, the processor unit 102, the display unit 103 and the support portable module 101. The connecting cable 104 connects the endoluminal probe 100 with the processor unit 102 for data transmission and power supply. The processor unit 102 is connected with the display unit 103 to display image and other data obtained by the endoluminal probe 100. The components 100, 101, 102, 103 and 104 may vary in size, shape and length according to the integrated constituent components specifications like cabling materials, computer processors, transducer configuration or any other included components. The device described is intended for use in hospital environment, however, as it is self sufficient regarding image acquisition and anatomical structure intervention, its use in a hemodynamic laboratory or an operating room is not mandatory. The processor unit 102 can be connected with more simultaneous endoluminal probes 100 if needed for the intended procedure. The display unit 103 can be repeated in other display monitors placed in different locations in the room regarding the operator position. Furthermore, the display unit 103 can display the real-time three dimension, the two dimension and the Doppler images acquired from the endoluminal probe 100 and any other data collected from other monitoring systems as required.

Figure 2:
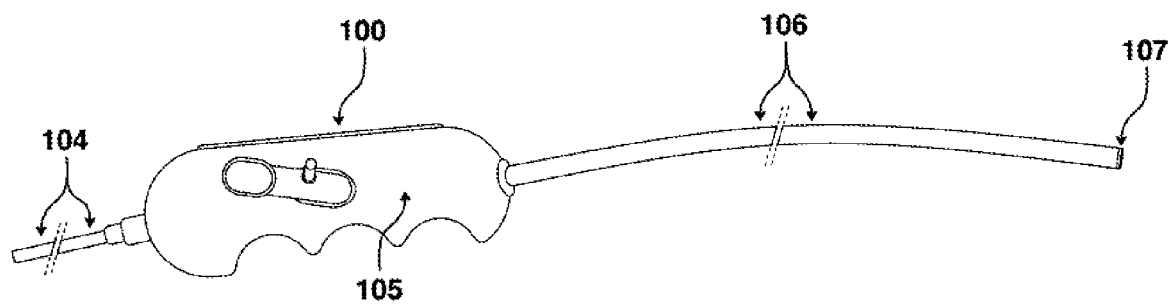
FIG. 2 is a schematic illustration of a side view of an embodiment of the endoluminal probe and its components.

FIG. 2 is a schematic illustration of a side view of the endoluminal probe 100 and its components, specifically the operating control element 105, the flexible cylindrical extension element 106 and the probe sensing and interface element 107 in accordance with an embodiment hereof. The operating control element 105 is designed for one hand operation to control the position of the flexible cylindrical extension element 106 and the probe sensing and interface element 107 in the desired anatomical vascular or cardiac structure. The flexible cylindrical extension element 106 is designed to be introduced into a peripheral major artery or vein throughout a vascular introducer and be manually advanced until the desired anatomical vascular or cardiac structure. The progression and regression in the vascular and cardiac structure of the flexible cylindrical extension element 106 and the probe sensing and interface element 107 is obtained by pushing and pulling of the endoluminal probe 100 throughout the vascular introducer. The direct vascular and cardiac structure interaction is possible with the other hand operation through the working channel that crosses the operating control element 105 until the distal opening in the probe sensing and interface element 107.

The operating control element 105 additionally incorporates the electrical motors and cables to operate the fine guiding of the flexible cylindrical extension element 106 and the probe sensing and interface element 107. The complete length of the flexible cylindrical element 106 and the connecting cable 104 is reduced by the dashed lines to comprise a comprehensive visualization of the endoluminal probe 100 components.

FIG. 3 is a schematic illustration of a top view of operating control element 105, with the representation of the working channel access inlet 108 and the air removal outlet 109. At the top of the operating control element 105 is the keyboard control buttons 110 for the image settings and the flexible cylindrical element 106 fine guiding orientation. The keyboard control buttons 110 may vary in configuration and position in the operating control element 105 according with the best operation function and ergonomic handling. The working channel access inlet 108 may have a different position in the operating control element 105 to improve the other hand handling. The air removal outlet 109 is needed to guarantee a complete blood filled and air free valve sealed working channel. The working channel access inlet 108 has a valve apparatus to minimize the blood leak and lost during the introduction and removal of the devices, appliances and instruments needed for the intended procedure. The working channel of the endoluminal probe 100 is a cylindrical pathway that starts in the working channel access inlet 108, crosses the operating control element 105 and continues thru the flexible cylindrical extension element 106 until the probe sensing and interface element 107 where it ends and opens. The dash point dash lines represent the explained pathway of the cylindrical working channel from the working channel access inlet 108 until the probe sensing and interface element 107. The complete length of the flexible cylindrical element 106 and the connecting cable 104 is reduced by the dashed lines to comprise a comprehensive visualization of the endoluminal probe 100 components.

FIG. 4 is a schematic illustration of the probe sensing and interface element 111 according to various embodiments.

FIG. 4.1 represents a sectional view of the probe sensing and interface element 111 in the progression mode. FIG. 4.2 represents a sectional view of the probe sensing and interface element 111 in the Intervention mode. FIG. 4.3 represents a frontal view of the probe sensing and interface element 111 in both progression and intervention modes. FIG. 4.4 represents a frontal and top view of the probe sensing and interface element 111 rotating mechanism. FIG. 4.5 represents a sectional view of an alternative hatch design for the probe sensing and interface element 111 in the progression mode. FIG. 4.6 represents a sectional view of an alternative hatch design for the sensing and interface element 111 in the Intervention mode. FIG. 4.7 represents a sectional view of an alternative design for the probe sensing and interface element 111 maintaining the same configuration in both progression and intervention modes. FIG. 4.8 represents a frontal view of the alternative design for the probe sensing and interface element 111.

The probe sensing and interface element 111 is composed by two components, the sensing element 112 and the probe working channel outlet 113 as represented in FIG. 4.1 to FIG. 4.8. The sensing element 112 in the probe sensing and interface element 111 integrates a miniaturized high definition three dimension ultrasonic transducer 114. The miniaturized high definition three dimension ultrasonic transducer 114 may be assembled in a Capacitive Micromachined Ultrasonic Transducer (CMUT) on complementary metal-oxide-semiconductor (CMOS) similar to the CMUT-on-CMOS chip described in the document "Compact, energy-efficient ultrasound imaging probes using cmut arrays with integrated electronics" (US 20130128702 A1) but with different arrangement of the array transmit and receive elements placed in a matrix fashion instead of a dual-ring fashion, with more transmit and receive elements for improved image definition, and an improved working channel design. The components design of the sensing element 112 may vary from the design represented in the figures without departing from the scope of the disclosure hereof.

FIG. 4.1 is a schematic illustration of a sectional view of the large caliber probe sensing and interface element 111 in the progression mode. During progression of the probe in the vascular introducer and vascular structure, the sensing element 112 is rotated downwards the probe working channel outlet 113 with the three dimension ultrasonic transducer 114 facing forward to sense and guide the progression of the endoluminal probe throughout the vessel until the desired anatomical location. In the progression mode the three dimension ultrasonic transducer 114 is rotated downwards to the working channel outlet 114 to preserve the same diameter as the flexible cylindrical element 106 during the progression of the probe until the anatomical endovascular or endocardiac structure to treat.

FIG. 4.2 is a schematic illustration of a sectional view of the probe sensing and interface element 111 in the Intervention mode. When the probe sensing and interface element 111 reaches the desired anatomical location to intervene, the sensing element 113 is rotated upwards 180° around a longitudinal axis of the probe to open the working channel outlet 113. In the Intervention mode the three dimension ultrasonic transducer 114 is positioned in an upper position for better angle to point the three dimension ultrasonic transducer 114 frontward in the same direction as the working channel outlet 113 to allow the anterior sensing and visualization of the working channel outlet 113 working field in the anatomical endovascular or endocardiac structure. Advantageously, the transducer being displaced laterally in respect of the line of sight improves the viewing angle, reduces ultrasonic 'shadows' and spurious reflections.

FIG. 4.3 is a schematic illustration of a frontal view of the probe sensing and interface element 111 in the progression mode 4.3a and intervention modes 4.3b. The probe sensing element 112 covers the working channel outlet 113 in the progression mode 4.3a and rotates upwards to expose the working channel outlet 113 in the intervention mode 4.3b. In particular, the rotation is 180° which maximises the view perspective and reduces ultrasound shadows or interferences. The endoluminal probe 100 may be assembled with smaller calibers applied to the flexible cylindrical extension element 106 and the probe sensing and interface element 107 but with the same structure configuration of all the remaining elements of endoluminal probe 100 in all its components although some components may have different shape, size and integrated components fitting the increasing miniaturization. Smaller caliber endoluminal probe 100 may be used for simple diagnostic and intervention procedures with smaller diameter access vascular port or as additional vascular port manipulation for more complex procedures combining two or more endoluminal probes 100 with either smaller or larger caliber endoluminal probes 100 with different arterial and venous vascular ports depending on the complexity of the procedure and the anatomical structures to treat.

FIG. 4.4 is a schematic illustration of a frontal and top view of the probe sensing and interface element 111 rotating mechanism for the three dimension ultrasonic transducer 114 to open the working channel outlet 113. The 180° rotation is operated by a gear wheel mechanism 115 activated by a rotatable cable. In the top view the electrical communication cable 116 for the three dimension ultrasonic transducer 114 is represented. The proportion of the probe working channel diameter in relation to the endoluminal probe 100 total diameter may vary but is designed to maximize the working channel diameter according to the present disclosure.

FIG. 4.5 is a schematic illustration of a sectional view of an alternative hatch design for the probe sensing and interface element 111 in the progression mode. During progression of the probe in the vascular introducer and vascular structure, the sensing element 112 is rotated inwards to the probe working channel outlet 113 with a (possibly lower definition) three dimension ultrasonic transducer 117 facing forward to sense and guide the progression of the endoluminal probe throughout the vessel until the desired anatomical location. In the progression mode the (possibly higher definition) three dimension ultrasonic transducer 114 is rotated inwards to the working channel outlet 113 to protect the higher definition transducer interface and to preserve the same diameter as the flexible cylindrical element 106 during the progression of the probe until the anatomical endovascular or endocardiac structure to treat.

FIG. 4.6 is a schematic illustration of a sectional view of an alternative hatch design for the probe sensing and interface element 111 in the Intervention mode. When the probe sensing and interface element 111 reaches the desired anatomical location to intervene, the sensing element 112 is rotated upwards around a transversal axis of the probe to open the working channel outlet 113. In the Intervention mode the low definition three dimension ultrasonic transducer 117 is facing upward and/or backwards and may be used for additional guidance and the higher definition three dimension ultrasonic transducer 114 is positioned frontward pointing the higher definition three dimension ultrasonic transducer 114 in the same direction as the working channel outlet 113 to allow the anterior sensing and visualization of the working channel outlet 113 working field in the anatomical endovascular or endocardiac structure where the intervention is to be carried out. Preferably, the rotation is more than 90° such that the higher definition transducer 114 rotates into the region where the intervention is to be carried out. Preferably, the rotation is less than 180° such that lower definition transducer 117 faces sideways in order to obtain a lateral view.

FIG. 4.7 is a schematic illustration of a sectional view of an alternative design for the probe sensing and interface element 111. The alternative design may be used for smaller caliber probe sensing and interface element 111 with smaller caliber flexible cylindrical extension element 106 and the probe sensing and interface element 107 but with the same structure configuration in all the remaining elements of endoluminal probe 100 in all its components except for the component 112 and 117 that may have different shape, size and integrated components. The smaller caliber probe sensing and interface element 111 can be used for simple diagnostic and intervention procedures with smaller diameter access vascular port or for additional vascular port manipulation for more complex procedures combining two or more endoluminal probes 100 with either small caliber or large caliber probe sensing and interface element 111 with different arterial and venous vascular ports depending on the complexity of the procedure and the anatomical structures to treat. The sensing element 112 in the smaller caliber probe sensing and interface element 111 maintains the same position in relation to the probe working channel outlet 113 in both progression and intervention modes. The smaller caliber probe sensing and interface element 111 integrate only a lower definition three dimension ultrasonic transducer 117.

FIG. 4.8 is a schematic illustration of a frontal view of the of the alternative design for the smaller caliber probe sensing and interface element 111 with the lower definition three dimension ultrasonic transducer 117 and the working channel outlet 113. The proportion of the probe working channel diameter in relation to the smaller caliber probe sensing and interface element 111 total diameter may vary. In this embodiment, the working channel is located in the endoluminal probe asymmetrically in respect of the longitudinal axis.

FIG. 5 is a schematic illustration of the superior view of the distal segment of the flexible cylindrical extension element 106 and the probe sensing and interface element 107 to further illustrate the degree of orientation in the horizontal axis allowed by the sequential arrangement of a series of flexibility units 118 in accordance with an embodiment hereof. The degree of horizontal axis orientation of the cylindrical extension element 106 and the probe sensing and interface element 107 may vary and be limited by the specific flexibility characteristics of the currently available and forthcoming transcatheter devices and specially designed surgical appliances and instruments for cylindrical small caliber working channels catheter based devices and surgical instruments. The orientation fine movement of the distal segment of the flexible cylindrical extension element 106 and the probe sensing and interface element 107 is cable operated and powered by electrical motors housed in the operating control element 105 and controlled with the keyboard control buttons 110.

Figure 6:
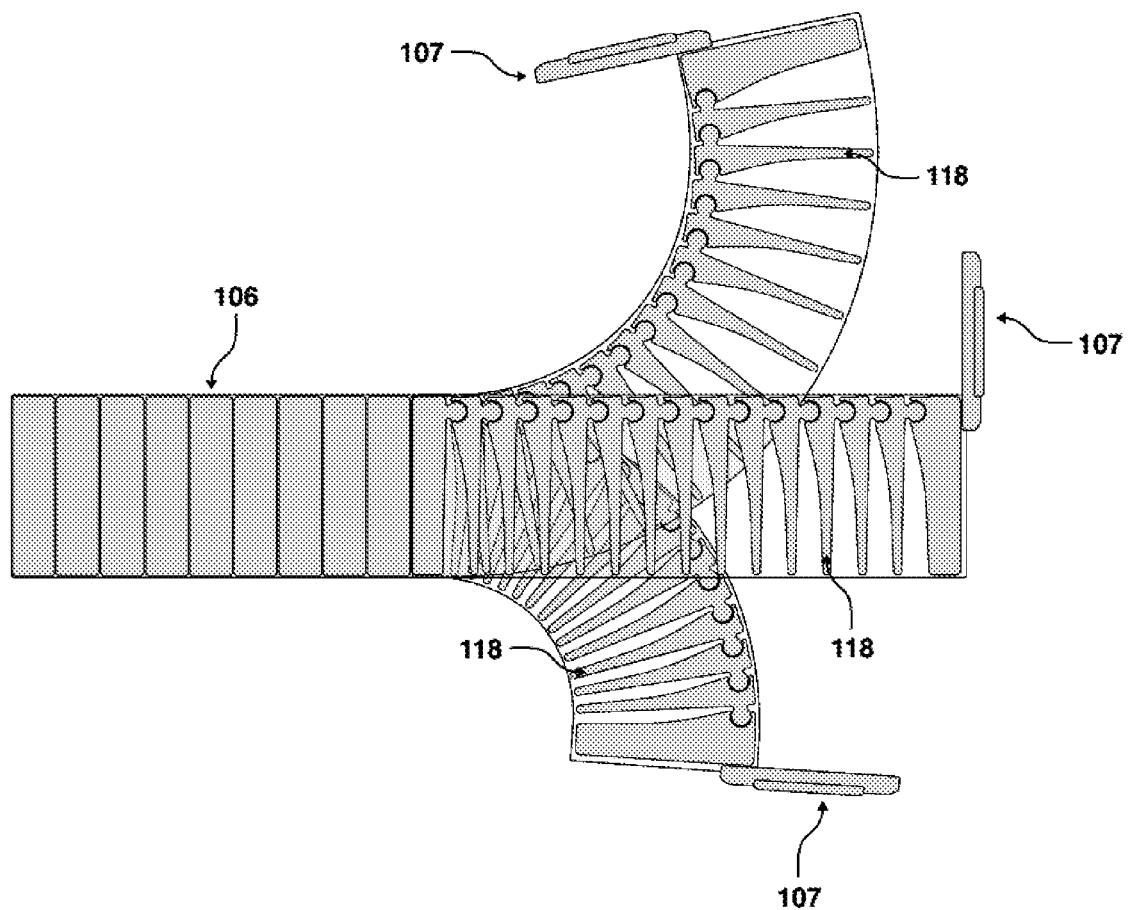

FIG. 6 is a schematic illustration of the lateral view of the distal segment of the flexible cylindrical extension element 106 and the probe sensing and interface element 107 to further illustrate the degree of orientation in the vertical axis allowed by the sequential arrangement of a series of flexibility units 118 in accordance with an embodiment hereof. The degree of vertical axis orientation of the cylindrical extension element 106 and the probe sensing and interface element 107 may vary and be limited by the specific flexibility characteristics of the currently available and forthcoming transcatheter devices and specially designed surgical appliances and instruments for cylindrical small caliber working channels catheter based devices and surgical instruments. The orientation fine movement of the distal segment of the flexible cylindrical extension element 106 and the probe sensing and interface element 107 is cable operated and powered by electrical motors housed in the operating control element 105 and controlled with the keyboard control buttons 110.

Figure 7:
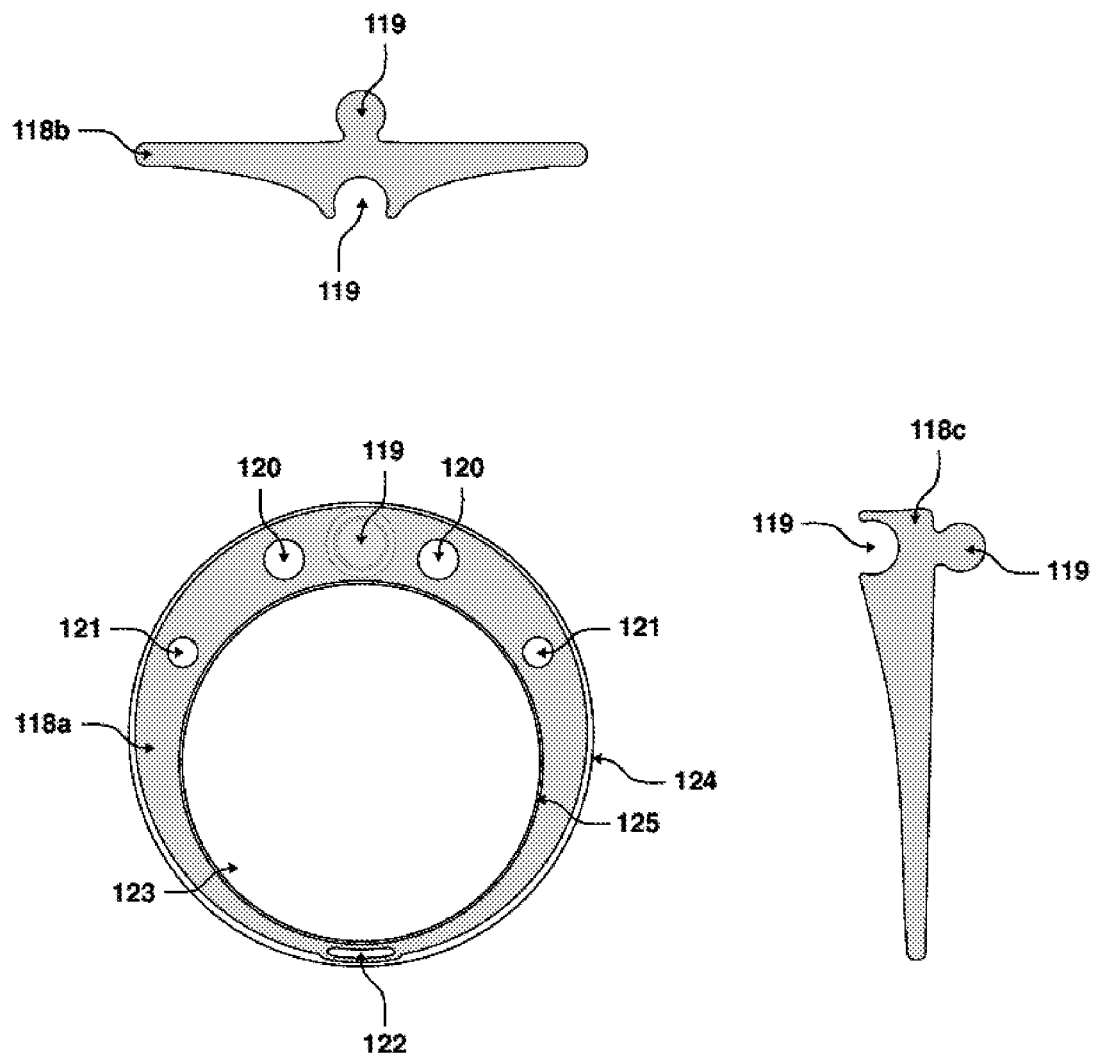
FIG. 7 is a schematic illustration of an embodiment of the flexibility unit.

FIG. 7 is a schematic illustration of flexibility unit 118 in the frontal view 118a, in the superior view 118b and in the lateral view 118c. The flexibility unit 118 is composed by a flexibility unit joint 119 that articulates with the next flexibility unit 118. In particular, the articulating joint is a ball joint.

In particular, the flexibility unit is ring-shaped, shaped as a hollow cylinder segment normal to the cylinder axis, i.e. a transversal hollow cylinder slice or a hollow disc, with the joint 119 being placed in one of the lateral parts of the ring in a face towards the next flexibility unit. The hollow of consecutive units defines a space. This space is the working channel 123. The working channel 123 is in a decentralized position in relation to the outer ring of the flexibility unit. This way, larger openings and joint elements may be placed in one of the lateral parts of the ring, maximizing the useful diameter of the working channel 123.

Further in particular, the ring may have a tapering thickness towards the end opposite the location of the joint 119, such that the flexibility of the sequential arrangement of a series of connected flexibility units is increased.

The flexibility unit 118 has communication openings 120 to allow the tunneled passage of the cable needed for the gear wheel mechanism 115 for mechanical rotation of the sensing element 112 in the probe sensing and interface element 111. The communication openings 120 additionally allow the tunneled passage of the communication cable 116 needed for power supply and data transmission between the sensing element 112 through flexible cylindrical extension element 106 until the operating control element 105 and the processor unit 102. The flexibility unit 118 furthermore has two horizontal axis orientation openings 121 and one vertical axis orientation opening 122 to allow the tunneled passage of the cables needed for the mechanical horizontal and vertical axis orientation of the sensing and interface element 111. The vertical and horizontal axis openings 121 and 122 are not represented in the superior view 118b and in the lateral view 118c.

The design of the flexibility unit 118 has a large working channel opening 123 that maximizes the working channel 123 diameter in relation to the outer diameter of the flexibility unit 118. The large working channel 123 is of utmost importance for the variety of procedures possible with the currently available and forthcoming transcatheter devices and specially designed surgical appliances and instruments for cylindrical small caliber working channels. The large working channel 123 is also essential for precise tactile feedback from the transcatheter devices and specially designed surgical appliances and instruments when interacting with the vascular and cardiac structures. The decentralized position of the working channel 123 in relation to the outer ring of the flexibility unit 118 is designed to maximize the working channel diameter with the greatest flexibility and tension resistance supported in the ampler portion where the flexibility unit joint 119 articulates.

In the frontal view illustration 118a the flexible outer coating sheath 124 and inner coating sheath 125 are represented. The flexible outer coating sheath 124 and inner coating sheath 125 materials may be polymeric membrane based, nevertheless the coating sheath materials may vary according to the state of the art materials for better flexibility, durability, sterilization compatibility and endovascular introduction and use. All the constituents of the flexibility unit 118 may vary in shape, materials and methods of fabrication and can be used as would be apparent to one of skill in the art in accordance with various embodiments of the present disclosure. The flexibility unit 118 material may be metallic (for example steel, aluminum or titanium alloys) or a hard polymeric material.

FIG. 8 is a schematic illustration of the endoluminal probe 100 in four potential clinical intervention and surgical scenarios. The potential clinical intervention and surgical scenarios represented in FIG. 8 are merely exemplary in nature and is not intended to limit the disclosure or the application and uses of the disclosure. According to the complexity of the procedure, the use of one or more endoluminal probes 100 thru additional arterial or venous vascular ports with another large caliber probe sensing and interface element 111 or a small caliber probe sensing and interface element 112 may be required. FIG. 8.1—the endoluminal probe 100 is introduced thru the femoral artery until the ascending aorta to preform a deployment of a transcatheter aortic valve 126. The endoluminal probe 100 allow a safe and accurate deployment of the transcatheter aortic valve 126 regarding the coronary ostium and the aortic valve annulus and the degree and location of the calcification in the native aortic valve. FIG. 8.2—the endoluminal probe 100 is introduced thru the femoral vein until the right atrium and thru the interatrial septum by transeptal puncture to the left atrium to preform a complex mitral valve repair with the implantation of transcatheter mitral ring 127, a transcatheter neocordae 128 and a leaflet transcatheter edge-to-edge stitch 129. The approach represented in FIG. 8.2 can also be used for deployment of a transcatheter mitral valve. To reduce the transcatheter mitral valve deployment system diameter the mitral valve ring may be previously secured with a transcatheter mitral ring 126 using the endoluminal probe 100 followed by the deployment of a smaller caliber transcatheter mitral valve. FIG. 8.3—the endoluminal probe 100 is introduced thru the femoral vein until the right atrium and thru the interatrial septum by transeptal puncture to the left atrium to preform the ablation pathways 130 in the left and right atriums to treat for atrial fibrillation using under direct three dimension reconstruction vision an ablation catheter 131. The orientation flexibility and the three dimension real-time image permitted by the endoluminal probe 100 allow a comprehensive left and right atrium ablation pathway. The endoluminal probe 100 additionally allows the continuous ablation transmurality evaluation required for successful atrial fibrillation treatment with the simultaneous two dimension echography images. FIG. 8.4—the endoluminal probe 100 is introduced thru the femoral artery thru the true lumen until the ascending aorta to identify the tear from an ascending aorta dissection and place by direct reconstruction three dimensional real-time vision a sealing endoprosthesis stent 132 to occlude and correct the dissection. The endoluminal probe 100 allows a secure size and location identification of the aortic intima tear and the location of the true and false lumen to clearly identify the proper site to deploy the sealing endoprosthesis stent 132. To treat the ascending aorta dissection as represented in FIG. 8.4 the placement of smaller endoprosthesis stents 133 in the true lumen guided under by direct reconstruction real-time vision with the endoluminal probe 100 may be needed for posterior expansion using the sandwich technic after the main sealing endoprosthesis stent 132 deployment to assure the perfusion of the aortic arch arteries. The procedure described in FIG. 8.4 using the endoluminal probe 100 can similarly be reproduced to treat other acute aortic syndromes and ascending aorta and aortic arch aneurisms. With the increasing complexity of the procedure, a less contracting heart may be desirable for a more secure structure manipulation and this can be obtained with transitory rapid pacing stimulation. If a standstill heart is required for longer periods of time, additionally or alternatively to the rapid pacing, the temporary use of an extracorporeal membrane oxygenator (ECMO) or a mini-extracorporeal circulation (MECC) thru the available arterial and venous ports may be necessary.

Figure 9:
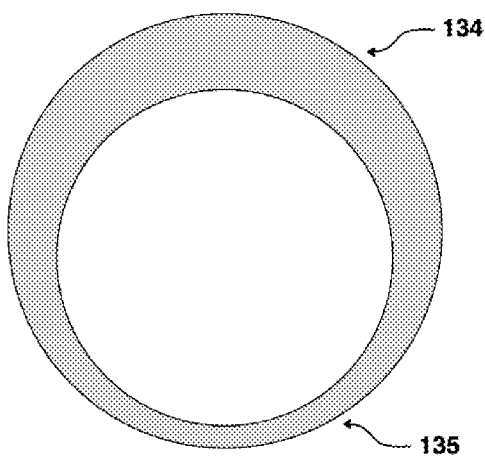
FIG. 9 is a schematic illustration of an embodiment of device in which the flexible tube has a working channel outlet on the distal end of the flexible tube thus defining a ring-shaped surface, wherein the working channel longitudinal axis is off-centred in respect of the flexible tube longitudinal axis, thus defining two sections of said ring-shaped surface, a wider section (134) and a narrower section (135), for example wherein the hatch door can be placed or coupled at said wider section of the ring-shaped surface of the distal end of the flexible tube.

FIG. 9 is a schematic illustration of a cross section of an embodiment of the endoluminal probe 100 to identify the location of the wider 134 and narrower 135 sections It is disclosed a device for intra-vascular and intra-cardiac access for image acquisition and surgical intervention comprising an endoluminal probe that connects with a processor and display unit, wherein the endoluminal probe has a probe component designed to be introduced in a peripheric vascular artery or vein to access the endovascular and endocardiac structures. The probe component has a distal mechanically controlled flexibility to maneuver and direct the distal portion of the probe inside the endovascular and endocardiac structures. The probe component has an elongated cylindrical lumen or working channel having a distal end and a proximal end. The probe distal component has a vision module comprising three dimension high-resolution ultrasonic transducer for image acquisition.

It is also disclosed a device wherein the endoluminal probe comprise: a plurality of flexibility units disks spaced along the distal portion of the probe length.

A method of operating the embodiments of the disclosed device in a endovascular or endocardiac structure filled with blood and with beating heart may comprise: Inserting a enclosed lumen through a single vascular port, wherein the lumen or working channel comprises a distal portion and a proximal portion; Obtaining a visual image of the environment surrounding the distal portion of the lumen during and after insertion; Opening the distal portion of the lumen to expose the vision module and working channel outlet; Rotating the vision module along the longitudinal axis of the lumen and vertically from the distal portion of the lumen.

The term "comprising" whenever used in this document is intended to indicate the presence of stated features, integers, steps, components, but not to preclude the presence or addition of one or more other features, integers, steps, components or groups thereof.

The disclosure should not be seen in any way restricted to the embodiments described and a person with ordinary skill in the art will foresee many possibilities to modifications thereof. The above described embodiments are combinable. The following claims further set out particular embodiments of the disclosure.

The invention claimed is:

1. A device for an intra-cardiac and intra-vascular surgical procedure comprising a surgical endoluminal ultrasound probe, said probe comprising:
   a flexible tube having a longitudinal hollow along a longitudinal axis of the flexible tube which defines a working channel for receiving and guiding transcatheter devices or instruments for the intra-cardiac and intra-vascular surgical procedure,
   a hatch door having a hinge, and
   an ultrasonic transducer for capture of data processable into three-dimensional (3D) images,
   an embedded motor cable operatively connected for opening or closing the hinge of the hatch door,
   a sequential arrangement of a plurality of ring-shaped units along a distal part of the flexible tube, wherein the embedded motor cable has an end attached to the most distal ring-shaped unit,
   wherein the flexible tube has a working channel outlet on a distal end of the flexible tube,
   wherein the hatch door is hingedly coupled to the distal end of the flexible tube by the hinge for opening and closing the working channel outlet, wherein the hinge rotates the hatch door 180° about an axis parallel to the longitudinal axis of the flexible tube between closed and open positions,
   wherein the ultrasonic transducer is placed at a forward-facing part of the hatch door and is positionable so as to be displaced laterally in respect of a line of sight defined by the working channel, within confines of intra-cardiac and intra-vascular locations in which the flexible tube is disposable in order to improve the viewing angle, reduce ultrasonic shadows and spurious reflections.

2. The device according to claim 1, wherein the flexible tube has the working channel outlet on the distal end of the flexible tube thus defining a ring-shaped surface, wherein a longitudinal axis of the working channel is off-centred in respect of a longitudinal axis of the flexible tube, thus defining two sections of said ring-shaped surface, a wider section and a narrower section, wherein the hatch door is disposed at the distal end of the flexible tube at said wider section of the ring-shaped surface.

3. The device according to claim 2, wherein the ring-shaped surface is annular and bounded by two non-concentric circles defined respectively by the flexible tube and the longitudinal hollow.

4. The device according to claim 1, wherein said probe further comprises an embedded motor cable operatively connected for opening or closing the hinge of the hatch door.

5. The device according to claim 4, further comprising a wheel gear mechanism that rotationally couples the motor cable and the hatch door.

6. The device according to claim 1, wherein each unit comprises a ball-joint and is coupled with an adjoining unit by said ball-joint.

7. The device according to claim 1, wherein the flexible tube has a working channel inlet on a proximal end of the flexible tube.

8. The device according to claim 7, comprising a handle for the flexible tube on the proximal end of the flexible tube, wherein the working channel inlet is comprised in said handle.

9. The device according to claim 8, wherein the handle comprises one or more motors for actuating motor cables, an electronic circuit for controlling said motors and at least one user controls for inputting control of said electronic circuit.

10. The device according to claim 9, wherein said handle comprises terminating connections of the motor and electric cables of the flexible tube.

11. The device according to claim 8, wherein said handle comprises a valve at the working channel inlet for minimizing blood leaks.

12. The device according to claim 8, wherein said handle further comprises an air removal outlet.

13. The device according to claim 1, comprising a handle on a proximal end of the flexible tube, wherein said handle comprises an electronic circuit and user controls for inputting control of said electronic circuit,
   said electronic circuit being configured to control at least one of image parameters of the ultrasonic transducer placed at the distal end of the flexible tube and the flexibility of the distal end of the flexible tube, and combination thereof.

14. The device according to claim 1, comprising a computer for processing data from the ultrasonic transducer and a display for displaying three-dimension images from the ultrasonic transducer.

15. The device according to claim 1, wherein each of the plurality of ring-shaped units comprises a ball-joint and is coupled with an adjoining unit by said ball-joint.

16. The device according to claim 1, wherein the flexible tube has a proximal end, the device further comprising a sequential arrangement of interlocked slidably disposed units wherein the slideably disposed units have a comparatively lower flexibility than the sequential arrangement of ring-shaped units along the distal part of the flexible tube.

17. The device according to claim 1, wherein the flexible tube has a working channel inlet and an air channel outlet adjacent a proximal end thereof, the device further comprising:
   a valve at the working channel access inlet configured to minimize blood leak during introduction and removal of the transcatheter devices or instruments for the intra-cardiac and intra-vascular surgical procedure, the valve, the air channel outlet, and the hatch door cooperating to define a blood filled and air free working channel for the flexible tube.

18. A device for an intra-cardiac and intra-vascular surgical procedure comprising a surgical endoluminal ultrasound probe, said probe consisting of:
   a flexible tube having a longitudinal hollow along a longitudinal axis of the flexible tube which defines a working channel for receiving and guiding transcatheter devices or instruments for the surgical procedure,
   a hatch door having a hinge, and
   an ultrasonic transducer for capture of data processable into three-dimensional (3D) images,
   an embedded motor cable operatively connected for opening or closing the hinge of the hatch door,
   a sequential arrangement of a plurality of ring-shaped units along a distal part of the flexible tube, wherein the embedded motor cable has an end attached to the most distal ring-shaped unit,
   wherein the flexible tube has a working channel outlet on a distal end of the flexible tube,
   wherein the hatch door is hingedly coupled to the distal end of the flexible tube by the hinge for opening and closing the working channel outlet, wherein the hinge rotates the hatch door 180° about an axis parallel to the longitudinal axis of the flexible tube between closed and open positions,
   wherein the ultrasonic transducer is placed at a forward-facing part of the hatch door and is positionable so as to be displaced laterally in respect of a line of sight defined by the working channel, within confines of intra-cardiac and intra-vascular locations in which the flexible tube is disposable in order to improve the viewing angle, reduce ultrasonic shadows and spurious reflections.

19. The device according to claim 18, wherein each of the plurality of ring-shaped units comprises a ball-joint and is coupled with an adjoining unit by said ball-joint.

20. A device for an intra-cardiac and intra-vascular surgical procedure comprising a surgical endoluminal ultrasound probe, said probe comprising:
   a flexible tube having a longitudinal hollow along a longitudinal axis of the flexible tube which defines a working channel for receiving and guiding transcatheter devices or instruments for the intra-cardiac and intra-vascular surgical procedure,
   a hatch door, and
   an ultrasonic transducer for capture of data processable into three-dimensional (3D) images,
   wherein the flexible tube has a working channel outlet on a distal end of the flexible tube,
   wherein the hatch door is hingedly coupled to the distal end of the flexible tube by a hinge for opening and closing the working channel outlet, wherein the hinge rotates the hatch door 180° about an axis parallel to the longitudinal axis of the flexible tube between closed and open positions,
   wherein the ultrasonic transducer is placed at a forward-facing part of the hatch door and is positionable so as to be displaced laterally in respect of a line of sight defined by the working channel, within confines of intra-cardiac and intra-vascular locations in which the flexible tube is disposable in order to improve the viewing angle, reduce ultrasonic shadows and spurious reflections, wherein the distal part of the flexible tube comprises a sequential arrangement of a plurality of ring-shaped units along the flexible tube, and wherein each unit comprises a ball-joint and is coupled with an adjoining unit by said ball-joint.

* * * * *